United States Patent
Govari et al.

(10) Patent No.: US 10,299,699 B2
(45) Date of Patent: May 28, 2019

(54) COMPUTERIZED TOMOGRAPHY IMAGE CORRECTION

(71) Applicant: Biosense Webster (Israel) Ltd., Yokneam (IL)

(72) Inventors: Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 15/362,518

(22) Filed: Nov. 28, 2016

(65) Prior Publication Data
US 2018/0146883 A1 May 31, 2018

(51) Int. Cl.
| | |
|---|---|
| *A61B 5/06* | (2006.01) |
| *A61B 6/00* | (2006.01) |
| *A61B 6/03* | (2006.01) |
| *G06T 7/00* | (2017.01) |
| *G06T 17/20* | (2006.01) |

(Continued)

(52) U.S. Cl.
CPC .............. *A61B 5/066* (2013.01); *A61B 5/062* (2013.01); *A61B 6/03* (2013.01); *A61B 6/466* (2013.01); *A61B 6/5247* (2013.01); *G06T 7/0012* (2013.01); *G06T 17/20* (2013.01); *A61B 6/032* (2013.01); *A61B 6/5258* (2013.01); *A61B 34/20* (2016.02); *A61B 2090/367* (2016.02);

(Continued)

(58) Field of Classification Search
CPC ........... A61B 5/066; A61B 5/062; A61B 6/03; A61B 6/466; A61B 6/5247; A61B 2090/367; G06T 7/0012; G06T 17/20; G06T 2207/10081; G06T 2210/41
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| | (Continued) | |

FOREIGN PATENT DOCUMENTS

| | | | | |
|---|---|---|---|---|
| DE | 102011087357 A1 * | 5/2013 | ......... | A61B 1/00009 |
| EP | 2 554 103 | 2/2013 | | |
| | (Continued) | | | |

OTHER PUBLICATIONS

English Translation of DE 102011087357 A1.*
European Search Report dated Apr. 25, 2018, Application No. EP 17 20 3897.

*Primary Examiner* — Jon Chang (57) ABSTRACT

Methods, apparatuses and computer program products implement embodiments of the present invention that include receiving, from an imaging system operating in an image coordinate system, a three-dimensional image of a body cavity including open space and body tissue, and receiving, from a medical probe having a location sensor and inserted into the body cavity, a signal indicating a location of a distal tip of the medical probe in a sensor coordinate system. The image coordinate system is registered with the sensor coordinate system so as to identify one or more voxels in the three-dimensional image at the indicated location, and when the identified voxels have density values in the received three-dimensional image that do not correspond to the open space, the density values of the identified voxels are updated to correspond to the open space.

17 Claims, 5 Drawing Sheets

(51) Int. Cl.
*A61B 90/00* (2016.01)
*A61B 34/20* (2016.01)

(52) U.S. Cl.
CPC .......... *A61B 2090/3762* (2016.02); *G06T 2207/10081* (2013.01); *G06T 2210/41* (2013.01)

(56) References Cited

U.S. PATENT DOCUMENTS

| | | |
|---|---|---|
| 5,558,091 A | 9/1996 | Acker et al. |
| 6,172,499 B1 | 1/2001 | Ashe |
| 6,177,792 B1 | 1/2001 | Govari et al. |
| 6,690,963 B2 | 2/2004 | Ben-Haim et al. |
| 6,788,967 B2 | 9/2004 | Ben-Haim et al. |
| 2010/0030064 A1* | 2/2010 | Averbuch ............... A61B 6/032 600/424 |
| 2013/0018255 A1* | 1/2013 | Kitamura ........... A61B 1/00009 600/424 |
| 2014/0330115 A1* | 11/2014 | Schildkraut .......... A61B 6/5217 600/425 |
| 2015/0024337 A1* | 1/2015 | Blassnig ................ G06T 15/06 433/29 |
| 2015/0112196 A1* | 4/2015 | Tanaka .................. A61B 5/065 600/437 |
| 2016/0338776 A1* | 11/2016 | Jaramaz ................ G16H 50/50 |

FOREIGN PATENT DOCUMENTS

| | | |
|---|---|---|
| EP | 2 837 328 | 2/2015 |
| WO | WO 2007/135609 | 11/2007 |

* cited by examiner

COMPUTERIZED TOMOGRAPHY IMAGE CORRECTION

FIELD OF THE INVENTION

The present invention relates generally to medical imaging, and specifically to correcting a compromised computerized tomography image while performing an invasive medical procedure.

BACKGROUND OF THE INVENTION

Superimposing a real-time representation of a medical device, such as a catheter tracked by a medical imaging system (e.g., a computed tomography scanner) during a medical procedure, is known in the art. An image that was previously acquired from a medical imaging system can be used to generate a real-time guide (i.e., a "map") that enables an operator performing the medical procedure to navigate the medical device within a volume of interest in a body of a patient. In order for the superimposition to reflect the true position of the medical device within that volume of interest, it is typically required to register the coordinate system associated with the medical device with the coordinate system associated with the medical imaging system.

The description above is presented as a general overview of related art in this field and should not be construed as an admission that any of the information it contains constitutes prior art against the present patent application.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention, a method, including receiving, from an imaging system operating in an image coordinate system, a three-dimensional image of a body cavity including open space and body tissue, receiving, from a medical probe having a location sensor and inserted into the body cavity, a signal indicating a location of a distal tip of the medical probe in a sensor coordinate system, registering, by a processor, the image coordinate system with the sensor coordinate system so as to identify one or more voxels in the three-dimensional image at the indicated location, and when the identified voxels have density values in the received three-dimensional image that do not correspond to the open space, updating the density values of the identified voxels to correspond to the open space. In some embodiments, the imaging system includes a computed tomography scanner. In additional embodiments, the location sensor includes a magnetic field sensor.

In further embodiments, the method may include forming a correspondence between the density values and visual effects, wherein a given visual effect corresponds to a given density value indicating the open space. In supplemental embodiments, the visual effects may be selected from a group consisting of colors, shadings and patterns.

In embodiments where the method includes forming a correspondence between the density values and visual effects, the method may include, presenting the three-dimensional image on a display using the visual effects. In some embodiments, the given visual effect includes a first given visual effect, and wherein prior to updating the density values, presenting the three-dimensional image includes presenting, using a second given visual effect different from the first given visual effect, the one or more identified voxels. In additional embodiments, upon updating the density values, presenting the three-dimensional image may include presenting, using the first given visual effect, the one or more identified voxels.

There is also provided, in accordance with an embodiment of the present invention, an apparatus, including a medical probe configured to be inserted into a body cavity, a location sensor in the medical probe operating in a sensor coordinate system, and a processor configured to receive, from an imaging system operating in an image coordinate system, a three-dimensional image of the body cavity including open space and body tissue, to receive, from the medical probe, a signal indicating a location of a distal tip of the medical probe, to register the image coordinate system with the sensor coordinate system so as to identify one or more voxels in the three-dimensional image at the indicated location, and when the identified voxels have density values in the received three-dimensional image that do not correspond to the open space, to update the density values of the identified voxels to correspond to the open space.

There is additionally provided, in accordance with an embodiment of the present invention, a computer software product operated in conjunction with a probe that is configured for insertion into a body cavity of a patient and includes a location sensor operating in a sensor coordinate system, the product including a non-transitory computer-readable medium, in which program instructions are stored, which instructions, when read by a computer, cause the computer to receive, from an imaging system operating in an image coordinate system, a three-dimensional image of the body cavity including open space and body tissue, to receive, from the medical probe, a signal indicating a location of a distal tip of the medical probe, to register the image coordinate system with the sensor coordinate system so as to identify one or more voxels in the three-dimensional image at the indicated location, and when the identified voxels have density values in the received three-dimensional image that do not correspond to the open space, to update the density values of the identified voxels to correspond to the open space.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Medical images used during medical procedures on a body cavity may sometimes be compromised. For example, computerized tomography images from a computerized tomography scanner can be compromised due to factors such as incorrect settings of the scanner, patient movement, and dental work in proximity to the body cavity. The compromisation is typically presented as noise or clutter on the image.

Embodiments of the present invention provide methods and systems for correcting a compromised medical image such as a computed tomography image, also referred to herein as a three-dimensional image. As explained hereinbelow, a three-dimensional image of a body cavity comprising open space and body tissue is received from an imaging system operating in an image coordinate system, and a signal is received from a medical probe having a location sensor and inserted into the body cavity, the signal indicating a location of a distal tip of the medical probe in a sensor coordinate system. The image coordinate system is registered with the sensor coordinate system so as to identify one or more voxels in the three-dimensional image at the indicated location, and when the identified voxels have density values in the received three-dimensional image that do not correspond to the open space, the density values of the identified voxels are updated to correspond to the open space.

Medical imaging systems typically use different visual effects to present open space and body tissue. For example, a computed tomography system may present open space in black, hard body tissue in white and soft body tissue in (various shades of) gray. Since the distal tip of the medical probe can only be inserted into open space, systems implementing embodiments of the present invention can correct, on the three-dimensional image, any locations of the distal tip that are not presented as open space.

System Description

Figure 1A:
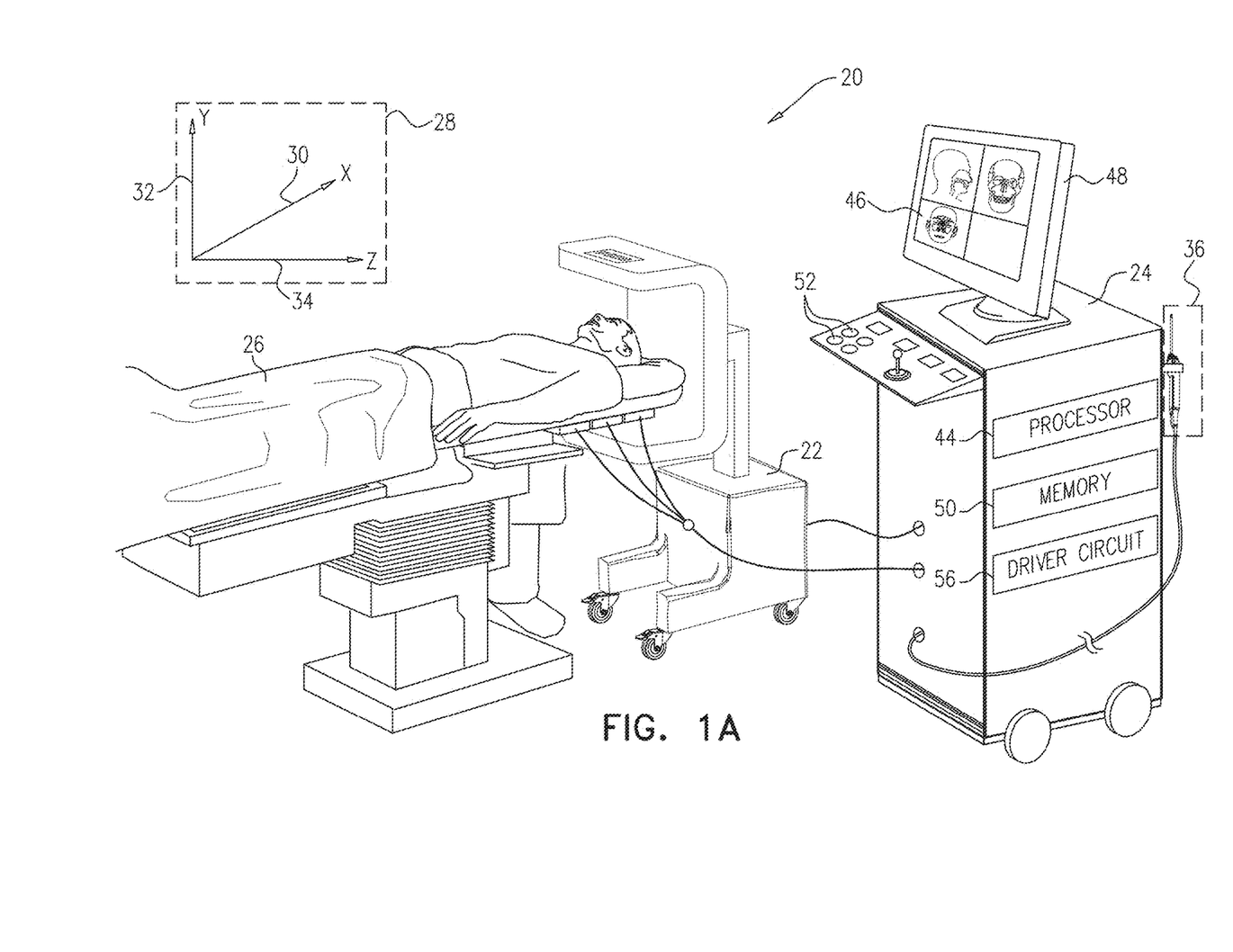
FIGS. 1A and 1B, referred to collectively as FIG. 1, are schematic pictorial illustrations of a medical system configured to correct, while using a medical probe to perform an invasive medical procedure, a compromised computerized tomography image, in accordance with an embodiment of the present invention.
Figure 1B:
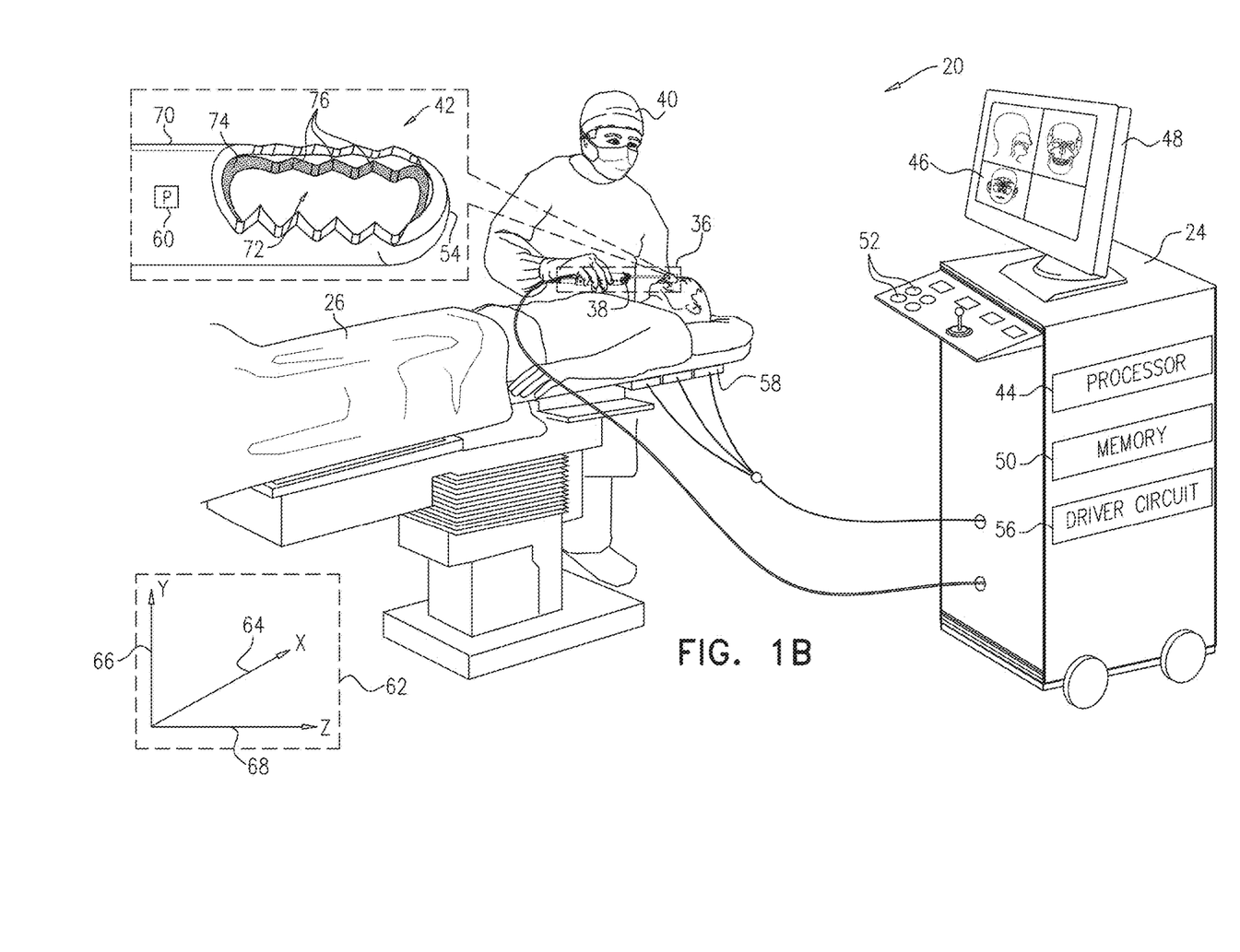

FIGS. 1A and 1B, referred to collectively as FIG. 1, are schematic pictorial illustrations of a medical system 20 configured to correct a compromised computerized tomography image while performing an invasive medical procedure, in accordance with an embodiment of the present invention. In the example shown in FIG. 1, medical system 20 comprises a medical imaging system comprising a computed tomography scanner 22, and control console 24, and a medical probe 36. In embodiments described herein, it is assumed that medical probe 36 is used for diagnostic or therapeutic treatment, such as minimally invasive catheter-based sinus surgery on a patient 26. Alternatively, medical probe 36 may be used, mutatis mutandis, for other therapeutic and/or diagnostic purposes.

As shown in FIG. 1A, prior to performing an invasive medical procedure on patient 26, computed tomography scanner 22 generates electrical signals comprising image data for a lumen (e.g., a nasal cavity or a paranasal sinus) of the patient, and conveys the generated image data to control console 24. Computed tomography scanner 22 generates the image data in an image coordinate system 28 comprising an X-axis 30, a Y-axis 32 and a Z-axis 34.

As shown in FIG. 1B, medical probe 36 comprises a handle that an operator 40 can grasp and manipulate in order to insert a distal end 42 of the medical probe into a lumen, such as a nasal cavity or a paranasal sinus, of patient 26. In the configuration shown in FIG. 1, control console 24 comprises a processor 44 that converts the received image data into an image 46, and presents the image as information regarding the medical procedure on a display 48.

Display 48 is assumed, by way of example, to comprise a flat panel display such as a liquid crystal display, a light emitting diode display, an organic light-emitting diode display or a plasma display. However, other display devices can also be employed to implement embodiments of the present invention. In some embodiments, display 48 may comprise a touchscreen that can be configured to accept inputs from operator 40, in addition to presenting image 46.

Based on the signals received from medical probe 36 and other components of medical system 20, control console 24 drives display 48 to update image 46 in order to present a current position of distal end 42 in the patient's body, as well as status information and guidance regarding the medical procedure that is in progress. Processor 44 stores data representing image 46 in a memory 50. In some embodiments, operator 40 can manipulate image 46 using one or more input devices 52. In embodiments where display 48 comprises a touchscreen display, operator 40 can manipulate image 46 via the touchscreen display.

Processor 44 typically comprises a general-purpose computer, with suitable front end and interface circuits for receiving signals from medical probe 36 and controlling the other components of control console 24. Processor 44 may be programmed in software to carry out the functions that are described herein. The software may be downloaded to control console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components.

In embodiments described herein, medical system 20 uses magnetic position sensing to determine position coordinates of a distal tip 54 of medical probe 36 inside patient 26. To implement magnetic based position sensing, control console 24 comprises a driver circuit 56 which drives field generators 58 to generate magnetic fields within the body of patient 26. Typically, field generators 58 comprise coils, which are placed below the patient at known positions external to patient 26. These coils generate magnetic fields in a predefined working volume that contains a lumen such as a paranasal sinus. A magnetic field sensor 60 (also referred to herein as location sensor 60) within distal end 42 of medical probe 36 generates electrical signals in response to the magnetic fields from the coils, thereby enabling processor 44 to determine the position of distal end 42 within the cardiac chamber.

Magnetic position tracking techniques are described, for example, in U.S. Pat. Nos. 5,391,199, 6,690,963, 5,443,489, 6,788,967, 5,558,091, 6,172,499 and 6,177,792, whose disclosures are incorporated herein by reference. The signals generated by magnetic field sensor 60 indicate the current location of distal tip 54 in a sensor coordinate system 62 comprising an X-axis 64, a Y-axis 66 and a Z-axis 68. In the example shown in FIG. 1, X-axis 64 generally corresponds to X-axis 32, Y-axis 66 generally corresponds to Y-axis 34 and Z-axis 68 generally corresponds to Z-axis 36.

In the example shown in FIG. 1B, distal end 42 comprises an outer tube 70 having a radial cutting window opening 72 in proximity to distal tip 54, and an inner tube 74 having a cutting blade 76. In operation, as cutting blade 76 traverses radial cutting window opening 72, the cutting blade can remove any body tissue protruding into the cutting window. In some embodiments, a motor (not shown) in handle 38 rotates inner tube 74 within outer tube 70, thereby enabling cutting blade 76 to traverse radial cutting window opening 72. While the example shown in FIG. 1B comprises a debrider tool configured to cut and remove body tissue, any other type of medical device comprising a location sensor 60 and configured to be inserted into patient 26 is considered to be within the spirit and scope of the present invention.

Figure 2:
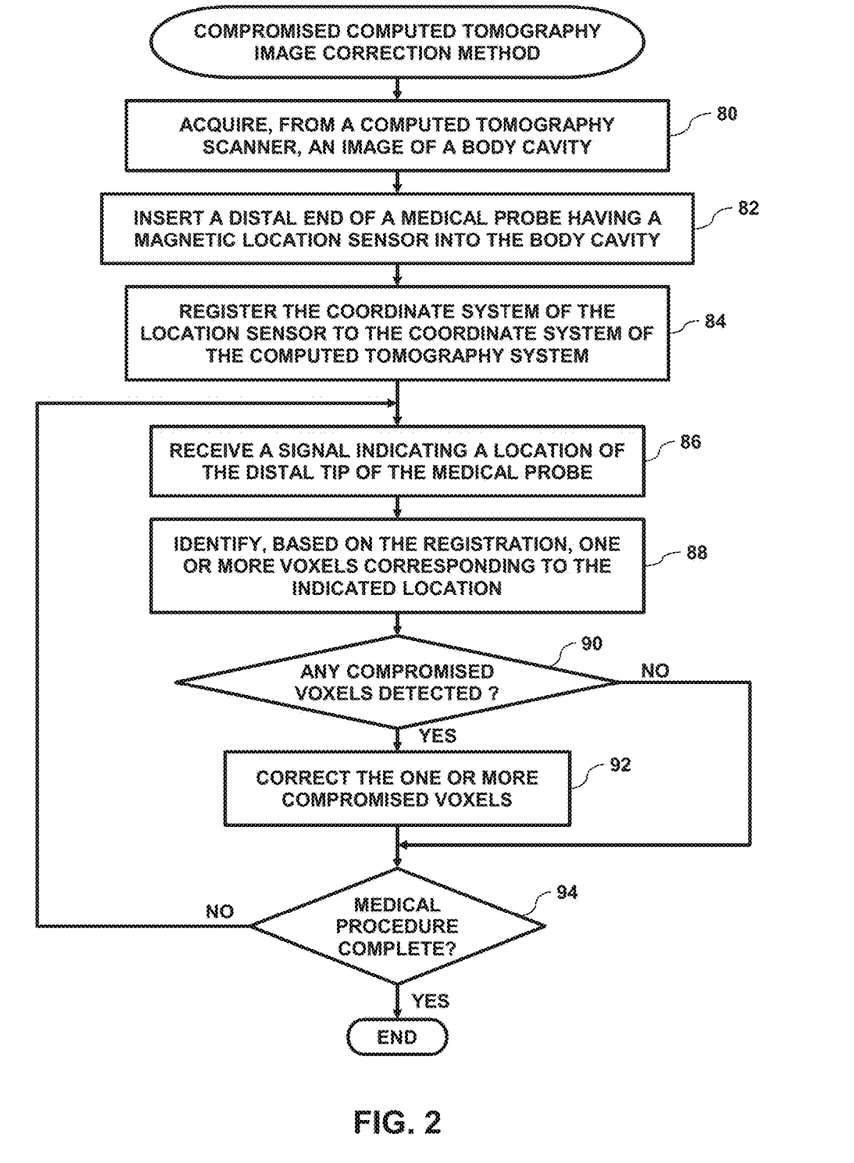
FIG. 2 is a flow diagram that schematically illustrates a method of correcting the compromised computed tomography image, in accordance with an embodiment of the present invention.

FIG. 2 is a flow diagram that schematically illustrates a method of correcting a compromised computed tomography image, in accordance with an embodiment of the present invention. In an acquiring step 80, processor 44 acquires image data from computed tomography scanner 22, stores the image data to memory 50, and generates, based on the acquired image data, a three-dimensional image. Step 80 is typically performed prior to a medical procedure to be performed on patient 26. To initiate the medical procedure, operator 40 manipulates handle 38 so that, in an insertion step 82, distal end 42 enters a body cavity in patient 26.

Figure 3:
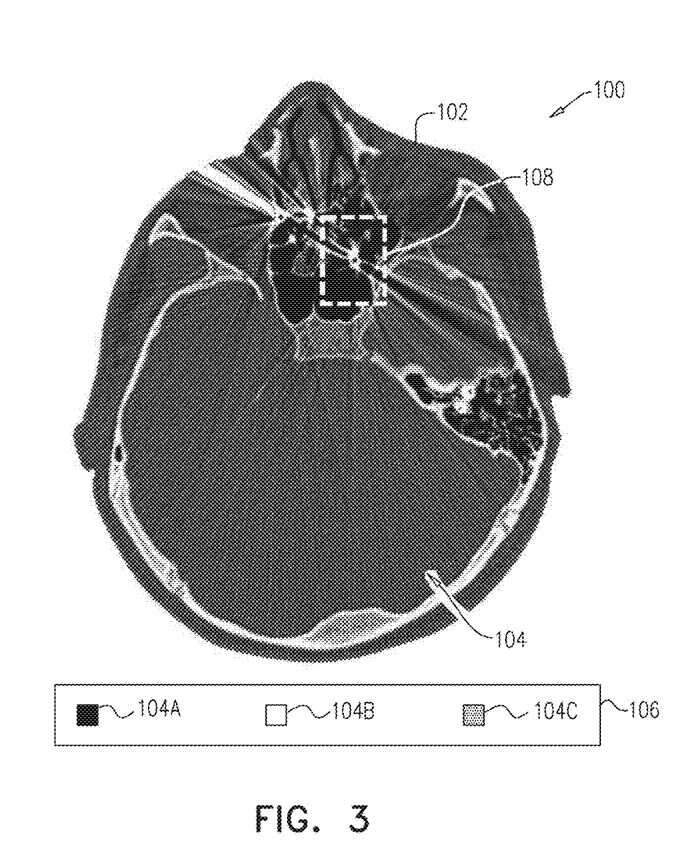
FIG. 3 is a schematic pictorial illustration showing an example of an image slice of a three-dimensional computed tomography image that generated in response to receiving image data from a computed tomography scanner, in accordance with an embodiment of the present invention.
Figure 4:
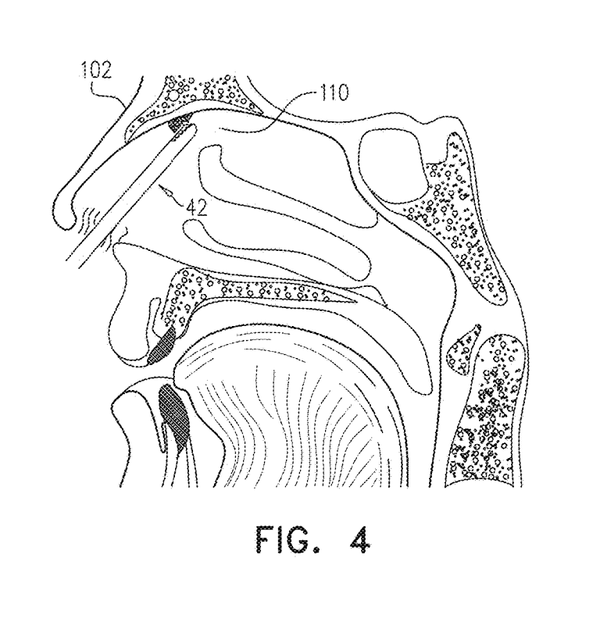
FIG. 4 is a schematic pictorial illustration showing a distal end of the medical prove inserted into a sinus cavity during the medical procedure, in accordance with an embodiment of the present invention.

FIG. 3 is a schematic pictorial illustration showing an image slice 100 of a three-dimensional computed tomography image that processor 44 generates in response to receiving the image data from computed tomography scanner 22, and FIG. 4 is a schematic detail view showing distal end 42 inserted into a sinus cavity 110, in accordance with embodiments of the present invention. In operation, processor 44 typically incorporates image slice 100 into image 46.

In the example shown in FIG. 3, image slice 100 comprises a two-dimensional "slice" of a head 102 of patient 26. Image slice 100 comprises voxels 104 of the three-dimensional image that correspond to three-dimensional locations in the computed tomography image of head 102. Processor 44 typically presents each given voxel 104 using different a visual effect that corresponds to the density detected at the three-dimensional location corresponding to the given voxel. Examples of densities include, but are not limited to, open space, hard body tissue and soft body tissue, and examples of visual effects include, but are not limited to, colors, shadings (e.g., different shades of gray) and patterns (e.g., gradients, pictures, textures, lines, dots and boxes).

As indicated by a legend 106, voxels 104 can be differentiated by appending a letter to the identifying numeral, so that the voxels comprise voxels 104A-104C. In the example shown in FIG. 3, voxels 104A indicate open space and are presented in black, voxels 104B indicate hard body tissue (e.g., bone) and are presented in white, and voxels 104C indicate soft body tissue (e.g., skin, cartilage, muscle and brain tissue) and are presented in gray. While embodiments herein describe image slice 100 comprising voxels 104 with three different visual effects (i.e. voxels 104A-104C), presenting the voxels with any number of visual effects representing any number of densities is considered to be within the spirit and scope of the present invention.

Image slice 100 also comprises a region of interest 108. As described in the description referencing FIGS. 5 and 6 hereinbelow, region of interest 108 includes interference that processor 44 can correct using embodiments described herein.

Returning to FIG. 2, in a registration step 84, processor 44 registers image coordinate system 28 to sensor coordinate system 62. Upon performing the registration, each three dimensional location indicated by a signal generated by magnetic field sensor 60 corresponds to one or more voxels 104. In a receiving step 86, processor 44 receives a signal from magnetic field sensor 60 indicating a location of distal tip 54, and in an identification step 88, the processor uses the registration to identify one or more voxels 104 that correspond to the indicated location.

In a first comparison step 90, if any of the one or more identified voxels are compromised (i.e., have density values indicating that they are not open space), then in a correction step 92, processor 44 corrects the compromised voxel(s). For example, if a given identified voxel 104 has a density value corresponding to hard tissue (i.e. the given identified voxel matches voxel 104B) or soft tissue (i.e., the given identified voxel matches voxel 104C) then processor 44 can update the density value to correspond to the open space (i.e., voxel 104A). In embodiments of the present invention, updating the one or more updated voxels in the image slice presented in image updates the three-dimensional computed tomography image stored in memory 50.

In operation, processor 44 presents image slice 100 on display 48 at the start of the medical procedure. As described supra, image slice 100 comprises a combination of voxels 104A indicating open space, voxels 104B indicating hard tissue and voxels 104C indicating soft tissue. Since distal tip 54 can only be present in open space, embodiments of the present invention correct any given voxel corresponding to a current location of distal tip 54 and having a density value that does not indicate open space. For example if processor 44 initially presents a given voxel 104 with a visual effect indicating that the given voxel is either soft or hard tissue (i.e., gray or black voxels 104 in the example shown in FIG. 3), and the processor subsequently detects that distal tip 54 is in a location corresponding to the given voxel, then the processor can update the given voxel by presenting the given voxel with a visual effect indicating open space (i.e., a given white voxel 104 in the example shown in FIG. 3).

In a second comparison step 94, if operator 40 has completed the medical procedure, then the method ends. However, if operator 40 has not yet completed the medical procedure, then the method continues with step 86. Returning to step 90, if none of the one or more identified voxels are compromised, then the method continues with step 94. While embodiments herein describe processor 44 using magnetic position sensing to correct a compromised computed tomography image, using other types of position sensing to correct other types of medical images is considered to be within the spirit and scope of the present invention.

Figure 5:
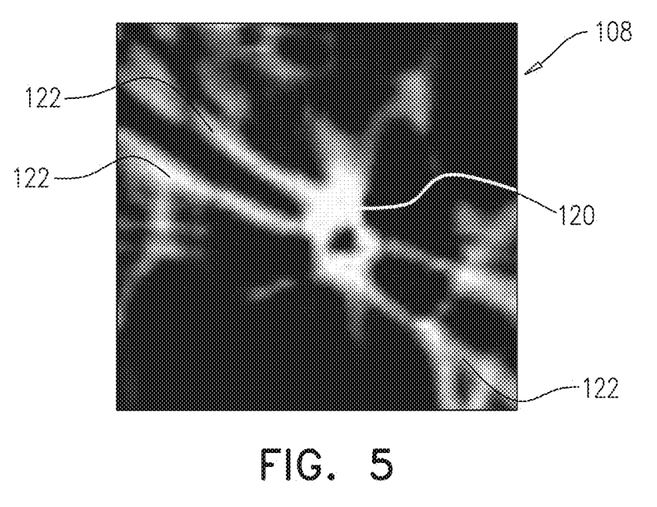
FIG. 5 is a schematic pictorial illustration showing a region of interest of the image slice prior to correcting the computed tomography image, in accordance with an embodiment of the present invention.

FIG. 5 is a schematic pictorial illustration showing region of interest 108 of image slice 100 prior to correcting the computed tomography image, in accordance with an embodiment of the present invention. In addition to voxels 104A, region of interest 108 comprises voxels 104B that indicate a hollow screw 120 and interference 122. In the example shown in FIG. 5, hollow screw 120 comprises an outer (typically circular) region of voxels 104B (i.e., metal in the screw) surrounding an inner region of voxels 104A (i.e., the hollow region of the screw), and interference 122 comprises "rays" of voxels 104B that radiate from hollow screw 120. In operation, computed tomography scanner may generate interference 122 due to factors such as the presence of dental work (e.g., tooth fillings) and movement of patient 26 while capturing the image data. As shown in FIG. 5, processor 44 presents interference 122 as hard and soft tissue.

Figure 6:
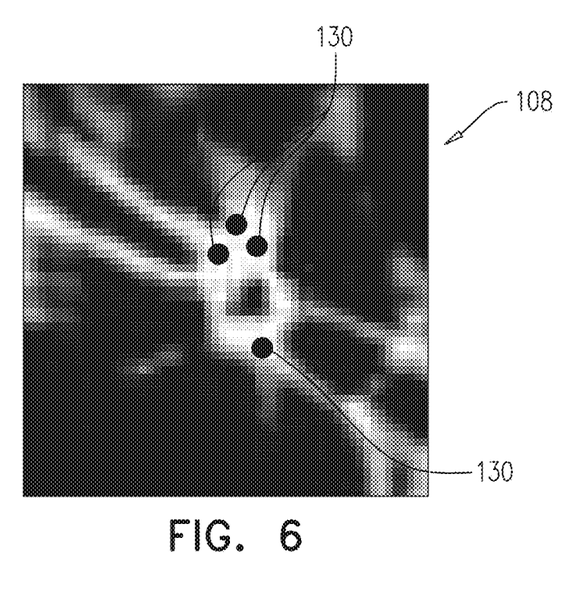
FIG. 6 is a schematic pictorial illustration showing the region of interest of the image slice subsequent to correcting the computed tomography image, in accordance with an embodiment of the present invention.

FIG. 6 is a schematic pictorial illustration showing region of interest 108 of image slice 100 subsequent to correcting the computed tomography image, in accordance with an embodiment of the present invention. As shown in FIG. 6, region of interest 108 comprises corrected regions 130. Regions 130 comprise regions which processor 44 assumes are open space because of the presence, detected by the processor, of distal tip 54.

Display 48 typically presents a subset of voxels 104 that processor 44 can update during a medical procedure using embodiments described herein. As described supra, image slice 100 comprises a two-dimensional "slice" of the three-dimensional image that processor 44 generates in response to receiving the image data from computed tomography scanner 22. Since operator moves distal end 42 in a three-dimensional space (i.e., three-dimensional coordinate systems 28 and 62), it will be understood that there can be additional voxels 104 (i.e., not included in the two-dimensional image slice currently being presented on display 48) whose respective density values are updated by processor 44 in response to detected locations of distal tip 54.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
receiving, from an imaging system operating in an image coordinate system, a three-dimensional image of a body cavity comprising open space and body tissue;
receiving, from a medical probe having a location sensor and inserted into the body cavity, a signal indicating a location of a distal tip of the medical probe in a sensor coordinate system;
registering, by a processor, the image coordinate system with the sensor coordinate system so as to identify one or more voxels in the three-dimensional image at the indicated location; and
when the identified voxels have density values in the received three-dimensional image that do not correspond to the open space, updating the density values of the identified voxels to correspond to the open space.

2. The method according to claim 1, wherein the imaging system comprises a computed tomography scanner.

3. The method according to claim 1, wherein the location sensor comprises a magnetic field sensor.

4. The method according to claim 1, further comprising forming a correspondence between the density values and visual effects, wherein a given visual effect corresponds to a given density value indicating the open space.

5. The method according to claim 4, wherein the visual effects are selected from a group consisting of colors, shadings and patterns.

6. The method according to claim 4, further comprising presenting the three-dimensional image on a display using the visual effects.

7. The method according to claim 6, wherein the given visual effect comprises a first given visual effect, and wherein prior to updating the density values, presenting the three-dimensional image comprises presenting, using a second given visual effect different from the first given visual effect, the one or more identified voxels.

8. The method according to claim 7, wherein upon updating the density values, presenting the three-dimensional image comprises presenting, using the first given visual effect, the one or more identified voxels.

9. An apparatus, comprising:
a medical probe configured to be inserted into a body cavity;
a location sensor in the medical probe operating in a sensor coordinate system; and
a processor configured:
to receive, from an imaging system operating in an image coordinate system, a three-dimensional image of the body cavity comprising open space and body tissue;
to receive, from the medical probe, a signal indicating a location of a distal tip of the medical probe;
to register the image coordinate system with the sensor coordinate system so as to identify one or more voxels in the three-dimensional image at the indicated location; and
when the identified voxels have density values in the received three-dimensional image that do not correspond to the open space, to update the density values of the identified voxels to correspond to the open space.

10. The apparatus according to claim 9, wherein the imaging system comprises a computed tomography scanner.

11. The apparatus according to claim 9, wherein the location sensor comprises a magnetic field sensor.

12. The apparatus according to claim 9, wherein the processor is configured to form a correspondence between the density values and visual effects, wherein a given visual effect corresponds to a given density value indicating the open space.

13. The apparatus according to claim 12, wherein the visual effects are selected from a group consisting of colors, shadings and patterns.

14. The apparatus according to claim 12, wherein the processor is configured to present the three-dimensional image on a display using the visual effects.

15. The apparatus according to claim 14, wherein the given visual effect comprises a first given visual effect, and wherein prior to updating the density values, the processor is configured to present the three-dimensional image by presenting, using a second given visual effect different from the first given visual effect, the one or more identified voxels.

16. The apparatus according to claim 15, wherein upon updating the density values, the processor is configured to present the three-dimensional image by presenting, using the first given visual effect, the one or more identified voxels.

17. A computer software product, operated in conjunction with a probe that is configured for insertion into a body cavity of a patient and includes a location sensor operating in a sensor coordinate system, the product comprising a non-transitory computer-readable medium, in which program instructions are stored, which instructions, when read by a computer, cause the computer:

to receive, from an imaging system operating in an image coordinate system, a three-dimensional image of the body cavity comprising open space and body tissue;

to receive, from the medical probe, a signal indicating a location of a distal tip of the medical probe;

to register the image coordinate system with the sensor coordinate system so as to identify one or more voxels in the three-dimensional image at the indicated location; and when the identified voxels have density values in the received three-dimensional image that do not correspond to the open space, to update the density values of the identified voxels to correspond to the open space.

\* \* \* \* \*